United States Patent [19]

Joffe

[11] Patent Number: 4,650,483
[45] Date of Patent: Mar. 17, 1987

[54] WASTE-CONTAINMENT GARMENT HAVING INTEGRALLY PROTECTED ADHESIVE FASTENERS

[75] Inventor: Frederick M. Joffe, Cincinnati, Ohio

[73] Assignee: The Procter & Gamble Company, Cincinnati, Ohio

[21] Appl. No.: 824,936

[22] Filed: Jan. 31, 1986

Related U.S. Application Data

[63] Continuation of Ser. No. 543,578, Oct. 19, 1983, abandoned.

[51] Int. Cl.⁴ .............................................. A61F 13/16
[52] U.S. Cl. .................................................. 604/390
[58] Field of Search ........................ 604/389, 390, 397

[56] References Cited

U.S. PATENT DOCUMENTS

| | | | |
|---|---|---|---|
| 3,638,651 | 2/1972 | Torr | 604/390 |
| 3,848,597 | 11/1974 | Endres | 604/390 |
| 3,901,237 | 8/1975 | Cepuritis et al. | 604/390 |
| 3,954,106 | 5/1976 | Tritsch | 604/390 |
| 4,014,340 | 3/1977 | Cheslow | 604/390 |
| 4,022,210 | 5/1977 | Glassman | 604/397 |
| 4,211,226 | 7/1980 | Schaar | 604/390 |
| 4,265,245 | 5/1981 | Glassman | 604/397 |

Primary Examiner—C. Fred Rosenbaum
Assistant Examiner—Sherri Vinyard
Attorney, Agent, or Firm—Thomas J. Slone; Frederick H. Braun; Richard C. Witte

[57] ABSTRACT

A waste-containment garment such as a disposable diaper or a disposable diaper insert which is fitted with integrally protected adhesive fasteners which do not extend outwardly from the edges of the garment. Each adhesive fastener comprises a pressure sensitive adhesive means disposed on an outer surface of the garment and an adhesive-release means disposed adjacent thereto on the same outer surface of the garment. Preferably such means are disposed on corner areas of the garment, and the garment is folded to associate each adhesive means in face-to-face adhered relation with its adjacent adhesive-release means until immediately prior to use of the garment. To use the garment, each adhesive means is peeled from its associated adhesive-release means so that it may be used for its intended purpose: e.g., to secure a diaper insert inside a diaper or overpant or the like; or to secure the back corners of a disposable diaper to the adjacent front corners of the disposable diaper. Diaper insert embodiments of the garment preferably have such means on each of their outwardly facing corners; and disposable diaper embodiments of the garment preferably have such means disposed on two of their inwardly facing corners.

8 Claims, 7 Drawing Figures

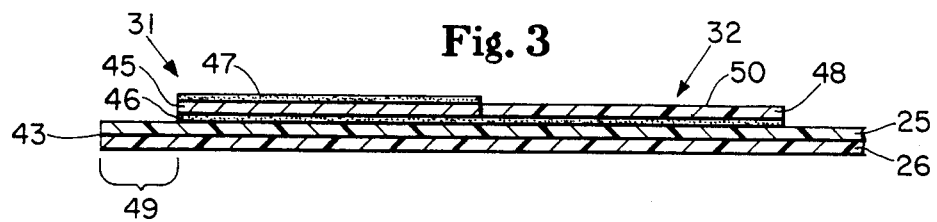
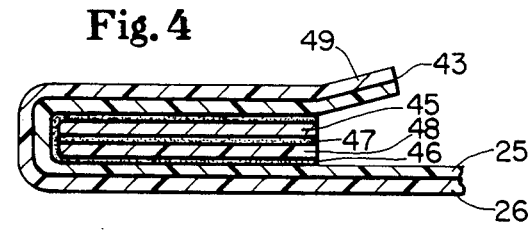
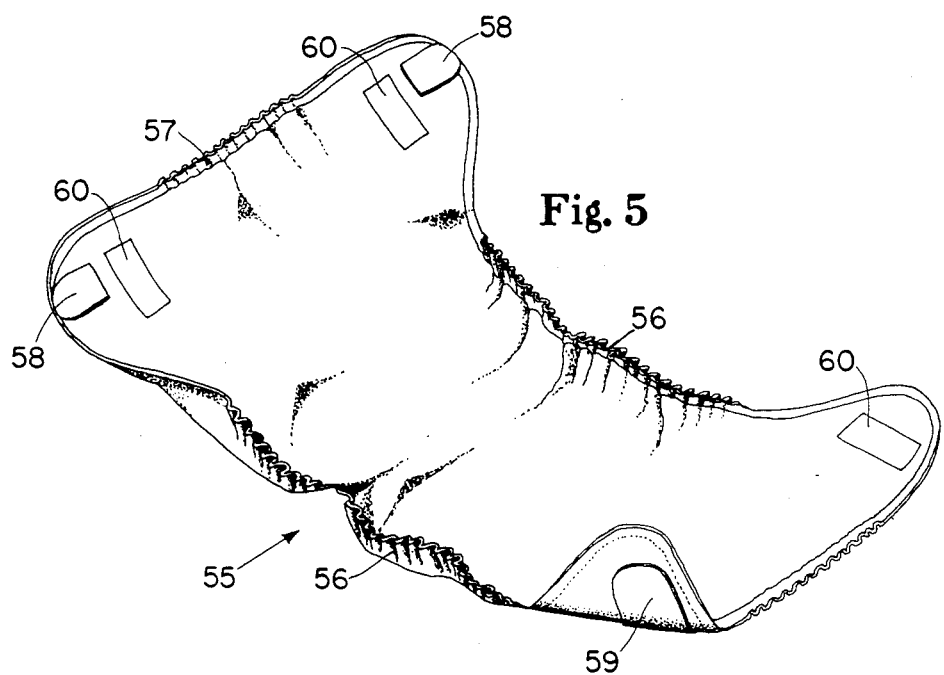

WASTE-CONTAINMENT GARMENT HAVING INTEGRALLY PROTECTED ADHESIVE FASTENERS

This application is a continuation, of application Ser. No. 543,578, filed Oct. 19, 1983. now abandoned.

DESCRIPTION

Technical Field

This invention pertains to a disposable waste-containment garment comprising an absorbent pad which garment has integral adhesive means for being secured during use: eg, means for securing the garment within another garment such as a diaper or overpant, or means for otherwise securing the garment on a user thereof as by fastening back corners thereof to front corners thereof. More specifically, this invention pertains to such garments having integrally protected adhesive fasteners which, in use, do not extend outwardly from the edges of the garment; and which, prior to use have their adhesive areas peelably adhered in face-to-face relation with an adjacent—preferably side-by-side—adhesive-release means or member. For example, a piece of release tape.

Background Art

A disposable diaper having integrally protected tape-tab fastener assemblies which, in use, have mother's-bond portions which extend beyond the edges of the diaper is disclosed in, for example, U.S. Pat. No. 3,848,594 which issued Nov. 19, 1974 to Kenneth Barclay Buell. The adhesively coated surface of the mother's-bond end of the tape fastener is releasably secured in face-to-face relation with a release-liner portion of the tape fastener to protect the adhesive prior to use.

A Disposable Diaper With A Supplemental Insert is disclosed in U.S. Pat. No. 4,022,210 which issued May 10, 1977 to Jacob A. Glassman, wherein the insert is provided with "adhesive spots 22 and 23 . . . [which] . . . are covered by sections of a covering material which can be easily stripped off . . . ": that is, removed and discarded.

A Disposable Diaper With Flap Covered Tape Fastener is described in U.S. Pat. No. 4,211,226 which issued July 8, 1980 to Charles H. Schaar. This comprises a sheet (eg, a backsheet) which sheet is slit and treated to form an integral releasable/peelable cover for an underlying pressure sensitive tape strip which is secured to underlying sturcture; ie, the absorbent pad of the diaper. In use, the peelable covers of such structures are not adhered in face-to-face relation with other structures as is provided by the present invention. That is, the adhesive-release means of the present invention such as discrete release tapes are secured to a surface of the garment in face-to-face relation both prior to and during use of such garment embodiments of the present invention: they do not merely remain attached by proximal ends thereof during use of the garment as in the Schaar structure.

Disclosure of the Invention

In accordance with one aspect of the invention, a disposable waste-containment garment comprising an outer envelope of sheet material, an absorbent pad enveloped thereby, and integrally protected adhesive fasteners is provided wherein each adhesive fastener comprises an adhesive means disposed on an outer surface of the envelope of sheet material of the garment, and an adhesive-release means disposed on the same outer surface and adjacent said adhesive means. Such means may comprise corner surface areas of said outer envelope which are coated with adhesive and release material, respectively, to enable face-to-face adhered but peelable association. Alternatively, either or both means may comprise discrete substrate members which are bonded to the envelope and which are appropriately coated and/or constituted to enable face-to-face adhered but peelable association. Prior to use, such garments preferably have their envelopes so folded that each adhesive means is peelably adhered in face-to-face relation with its respective adhesive-release means. Diaper insert embodiments of the invention preferably have their adhesive means and their adhesive-release means disposed on corner surface regions of the outwardly facing portion of the envelope; and, preferably, disposable diaper embodiments of the invention have their adhesive means and their adhesive-release means disposed on two corner surface regions of the envelope which, in use, face inwardly towards the body of the user. Additionally, such means are preferably sufficiently spaced from the corner edges of the envelope so that edge regions of the envelope may be grasped and pulled to peel the adhesive means from the adhesive-release means. Preferably, the envelope comprises a liquid impervious backsheet, and a liquid pervious topsheet which are sufficiently bonded together and to the core to provide the garment with sufficient structural integrity for its intended use. However, it is not intended to thereby limit the present invention to envelopes of only this configuration.

BRIEF DESCRIPTION OF THE DRAWINGS

While the specification concludes with claims particularly pointing out and distinctly claiming the subject matter regarded as forming the present invention, it is believed the invention will be better understood from the following description taken in conjunction with the accompanying drawings in which:

FIG. 3 is an enlarged scale, fragmentary sectional view taken along line 3—3 of FIG. 2 which section line extends through an adhesive fastener of the insert disposed on a corner surface region of the envelope of the insert.

FIG. 4 is an enlarged scale, fragmentary sectional view similar to FIG. 3 except it shows the corner portion of the envelope of the insert to be U-folded and with the adhesive means of the fastener adhered in face-to-face relation with its associated adhesive-release means.

FIG. 5 is a perspective view of an overpant which is adapted to accommodate a disposable insert embodiment of the present invention; eg, an insert such as shown in FIG. 1.

DETAILED DESCRIPTION OF THE INVENTION

Figure 1:
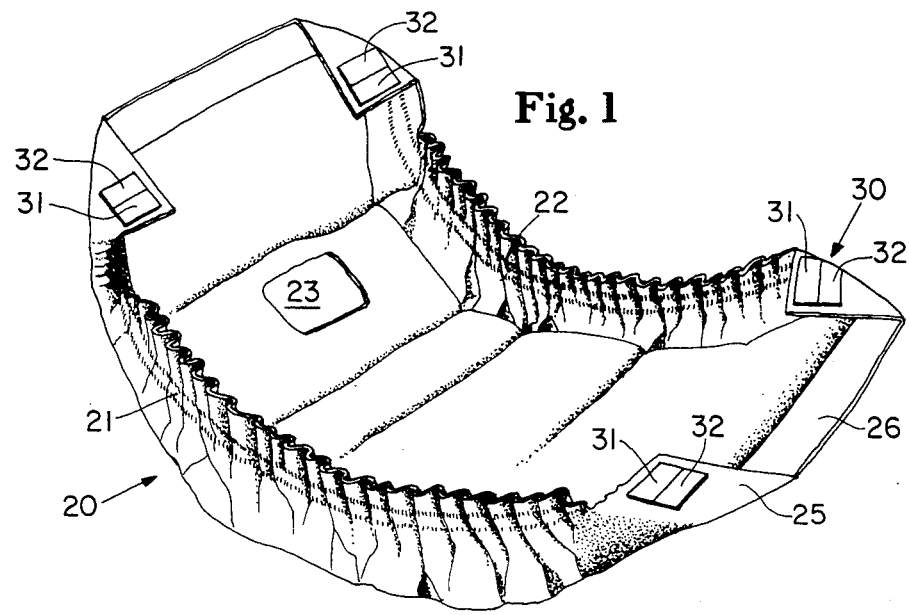
FIG. 1 is a perspective view of a disposable waste-containment diaper insert embodiment of the present invention wherein each outwardly facing corner is provided with an adhesive fastener in accordance with the present invention.

An exemplary garment which is an embodiment of the present invention is shown in FIG. 1 to be an elasticized disposable diaper insert 20 which comprises elasticized leg cuffs 21 and 22, an absorbent core 23, an envelope of sheet material which comprises a backsheet 25 of a liquid impervious thermoplastic film and a liquid pervious topsheet 26 which are perimetrically bonded together beyond the reaches of core 23, and an adhesive fastener 30 on each corner of backsheet 25. Each adhesive fastener 30 comprises an adhesive means 31 and an adhesive-release means 32.

Briefly, prior to use, adjacent means 31 and 32 of insert 20, FIG. 1, are peelably adhered in face-to-face relation to preserve the efficacy of the adhesive means 31. The adhesive means 31 are peeled from the adhesive-release means 32 to enable fastening the insert 20 in an overpant or inside a diaper with the adhesive means 31 as is more fully described hereinafter. This provides an assembly having a captive adhesive-release means which is permanently disposed on the same surface of the insert as the adhesive means of the fastener. Thus, no elements of the insert are removed therefrom at the time of application to a user; and the fastener elements have no unsecured lengths. Additionally, the fasteners have no portions which, in use, extend beyond the edges of the envelope of the insert as would be the case with tape-tab fasteners.

Figure 2:
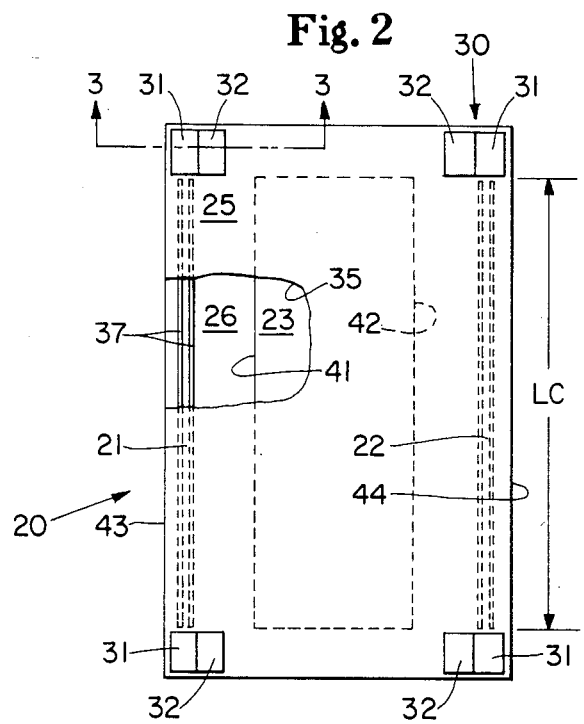
FIG. 2 is a plan view of the insert embodiment of FIG. 1 which view is taken looking at the side of the insert which, in use, faces outwardly: ie, away from the body of the user.

Referring now to FIG. 2, a portion of backsheet 25 of insert 20 has been torn away along line 35 to reveal the underlying structure which comprises core 23, topsheet 26, and two strands of elastic 37 in each of the cuffs 21 and 22 which are elasticized thereby. The longitudinal side edges of core 23 are designated 41 and 42; and the length of core 23 is designated LC. The longitudinal side edges of insert 20 are designated 43 and 44. It is, however, not intended to thereby limit the present invention to this particular construction.

FIG. 3 which is taken along section line 3—3 of FIG. 2 shows the construction of an adhesive fastener 30 in enlarged scale; and its disposition with respect to the adjacent longitudinal edge 43 of the insert which edge 43 happens to also be the composite of the longitudinal side edges of backsheet 25 and topsheet 26. As shown in FIG. 3, adhesive means 31 comprises a fastener substrate (eg, tape) 45 which is adhesively secured to an outwardly facing surface area of backsheet 25 with adhesive 46, and which is coated with a pressure sensitive adhesive 47. Similarly, adhesive-release means 32 is shown to comprise a release solution 48 which is also adhesively secured to backsheet 25 in side-by-side adjacency with fastener substrate 45 by adhesive 46. Release substrate 48 is made of material having an adhesive release surface property of is coated on its outwardly facing surface 50 with adhesive release material which enables adhesive 47 to be peelably adhered thereto prior to usage of insert 20. As is also shown in FIG. 3, fastener substrate 45 is spaced from edge 43 to provide a grasping edge portion 49 of the topsheet/backsheet composite to enable peeling fastener substrate 45 along with adhesive 47 from release substrate 48 as further described below.

In FIG. 4, the structure shown in FIG. 3 has been folded to secure substrates 45 and 48 in face-to-face relation with adhesive 47. Preferably, each corner of insert 20 is so folded and secured at the time of its manufacture in order to preserve the potential efficacy of adhesive 47 for later securing the insert inside an overpant garment or inside a diaper.

An exemplary substrate 45 comprises an uncoated paper tape which is available from Midtex, North Mankato, Minnesota (their Stock No. 1830). This substrate was coated on both sides with an adhesive Stock No. 4328 obtained from Century Adhesives, Columbus, Ohio, to provide adhesive coatings 46 and 47 having thicknesses of 0.8 mils and 1.5 mils, respectively. An exemplary release-tape for substrate 48 was obtained from Acra-Seal, Huntington Beach, Calif. (their Stock No. 9KO). However, it is not intended to thereby limit the present invention to these substrates and/or adhesives.

Fastener 30 has been described above as comprising an adhesive coated substrate and a release substrate which are secured in side-by-side relation to backsheet 25 with adhesive 46. Alternatively, the areas of backsheet 25 underlying the substrates 45 and 48 as shown in FIGS. 3 and 4 may be coated with adhesive and adhesive-release material, respectively. In this event, the substrates 45 and 48 per se would, of course, be dispensed with; or other means may be provided to enable refastenably/peelably adhering adhesive means 31 to an adjacent surface area of the envelope of the garment.

Referring back to FIGS. 1 and 2, an exemplary insert 20 was constructed in which the backsheet 25 is a matte-finish polyethylene film having a nominal thickness of about one mil (about 0.0254 mm), and overall length and width of about fifteen inches by about eight inches, respectively (about 38.1 by 20.3 cm, respectively) the topsheet 26 is a non-woven polypropylene having a nominal thickness of about twenty (20) mils, and length and width about equal to the corresponding dimensions of the backsheet; an air laid fibrous core 23 having a nominal weight of about 30.7 grams, a nominal caliper of about 7.1 mm, and length and width of about thirteen by four inches, respectively (about 33 by 10.2 cm, respectively); strands 37 of elastic having nominal unstretched thickness and width of about 0.2 and 2.4 mm, respectively, and which had been stretched about one-hundred-twenty-five percent (125%) prior to being adhesively secured to the backsheet, and prior to adhesively securing the topsheet to the backsheet whereby the longitudinal side edges of the insert (i.e., the elasticized leg cuffs 21 and 22) have nominal extensions (i.e., their available stretch as a percent of their elastically contracted length) of about one-hundred-twenty-five percent. Additionally, the core is enveloped with a low basis weight tissue paper not shown to provide structural integrity.

As further shown in FIG. 2, the elastic strands 37 extend longitudinally between the adhesive means 31, and the strands 37 are disposed adjacent the longitudinal side edges 43 and 44 of insert 20. In the exemplary insert, the inboard edge of the elastic strand 37 disposed closest to the absorbent core 23 is spaced therefrom about one-and-seven eighths inches (about 4.76 cm) whereby the elasticized leg cuffs—being relatively wide—can be contracted and stretched without having to induce crumpling or longitudinal compression of core 23. Thus, stretching induced tension is available for sealingly engaging the leg cuffs 21 and 22 with skin areas of a wearer rather than being vitiated by the resistance of the core to being longitudinally compressed. FIG. 2 also shows that portions of the adhesive means 31 are disposed in longitudinal alignment with the elastic strands 37, and that the adhesive means are longitudinally spaced a distance equal to the length LC of core 23. In the exemplary insert LC is about thirteen inches (about 33 cm) although it is not intended to thereby limit the present invention.

FIG. 5 is a perspective view of an exemplary overpant 55 in which inserts 20 may be secured and used. FIG. 5 shows overpant 55 having elasticized leg cuffs 56; elasticized waistbands 57; hook and loop type side-closure fastener means such as Velcro (registered trademark of Velcro USA Inc.) which comprise swatches 58 of hook-type fastener material which have been sewn to the inside of the back corners of the overpants and swatches 59 of loop-type fastener material which have been sewn to each outside front corner of the overpants but only one of which swatch 59 is visible in FIG. 1; and landing pads 60 disposed on each inside corner of the overpants and which are made from material which will provide releasable application thereto of the adhesive means 31 on insert 20. Such landing pads are preferably spaced equal to the uncontracted spacing of the adhesive means on insert 20 whereby, upon application of a liner 20 inside an overpant 55 to a wearer, the leg cuffs 21 and 22 of insert 20 are automatically properly tensioned in sealing relation with skin areas of the wearer. Such overpants preferably have a liquid impervious construction which may comprise a liquid impervious layer of material disposed outside of a soft fabric topsheet (i.e., innermost ply), and which may have a soft fabric backsheet (i.e., outmost ply) which may be decoratively adorned with lace and the like, not shown. An exemplary quality overpants comprising Velcro sideclosure means, elasticized leg cuffs, and an elasticized back-waistband is marketed in a variety of sizes by Nishiki K.K. under the Brand name of Semi Cot Proof in Japan. This has a generally liquid impervious construction although its leg cuffs are believed to be a breathable, porous construction. However, landing pads 60 are not part of the commercially available Semi Cot Proof overpants.

Figure 6:
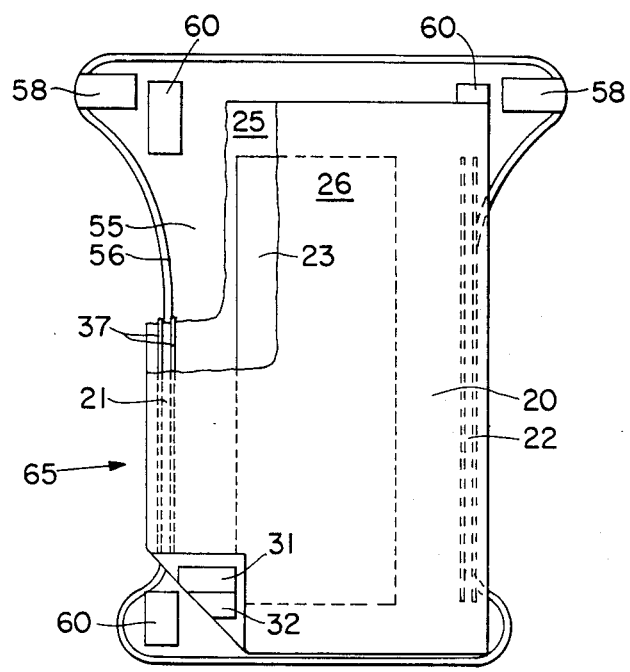
FIG. 6 is a plan view of an overpant like that shown in FIG. 5 with a fragmentary portion of a diaper insert like that of FIG. 1 superimposed thereon.

FIG. 6 is a composite plan view of an exemplary composite waste-containment garment 65 comprising an insert 20, FIG. 1, and overpant 55, FIG. 5, in assembled relation with the topsheet 26 of insert 20 facing upwardly, and with various portions torn away to reveal the underlying structure as described above. As shown in FIG. 6, insert 20 of exemplary composite waste-containment garment 65 is wider when stretched to remove its elastic induced contraction than the underlying structure of overpants 55. However, when applied to a user, the leg cuffs 21 and 22 of insert 20 are positioned to be inboard of the leg cuffs 56 of overpant 55.

Figure 7:
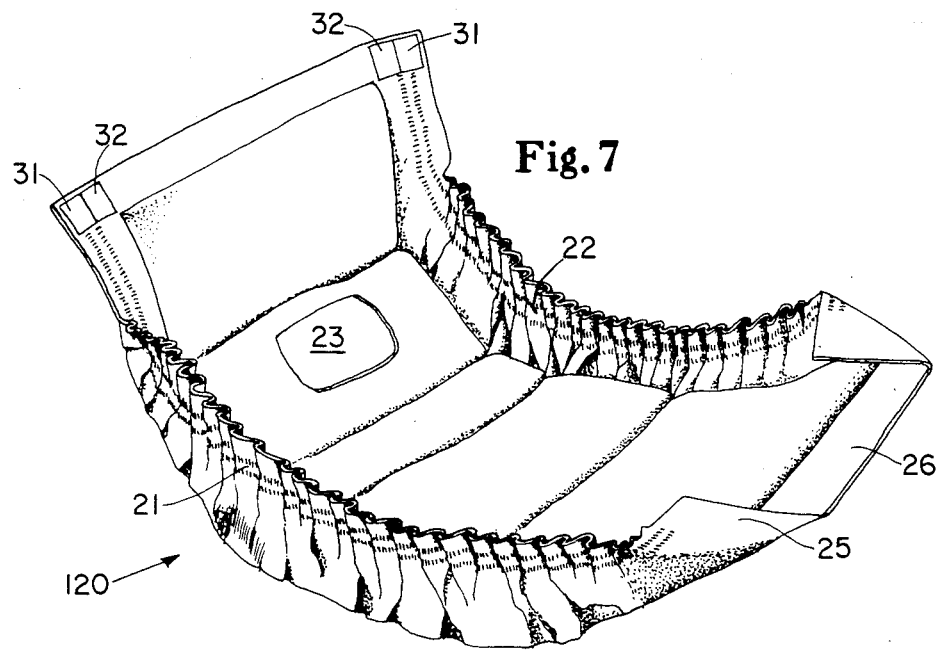
FIG. 7 is a perspective view of a disposable diaper embodiment of the present invention.

FIG. 7 is a perspective view of a disposable diaper 120 which is an embodiment of the present invention. Essentially, it is of the same construction as insert 20, FIGS. 1 and 2 except diaper 120 has adhesive fasteners 30 disposed on only the two back corners which face inwardly (ie, towards the wearer's body when applied to a user) whereas insert 20 has adhesive fasteners 30 on each of its four outwardly facing corners. The structural features and elements of diaper 120 which are the same as corresponding features and elements are identified by the same designators in the several views.

The back corners of diaper 120 are, preferably folded at the time of manufacture to adhere adhesive means 31 to their respective adjacent release means 32 in the manner indicated in FIG. 4. At the time of use, each adhesive means 31 is peeled from its adjacent release means 32 and adhered to a frontal area of backsheet 25: ie, the mother's-bond region of the diaper.

While particular embodiments of the present invention have been illustrated and described, it would be obvious to those skilled in the art that various other changes and modifications can be made without departing from the spirit and scope of the invention. It is intended to cover in the appended claims all such changes and modifications that are within the scope of this invention.

What is claimed is:

1. A disposable waste-containment garment comprising an envelope of flexible sheet material having longitudinal edges, an absorbent core wholly enclosed within said envelope, and a plurality of adhesive fasteners which do not extend beyond the edges of said envelope each of said adhesive fasteners comprising adhesive means and adhesive-release means in side by side adjacency with each other, said envelope defining an outside surface facing away from the wearer and an inside surface facing the wearer, said envelope being folded such that prior to use each adhesive means is peelably adhered to its respective adjacent adhesive-release means whereby said envelope may be unfolded for use by peeling said adhesive means from said adhesive release means, said envelope being sufficiently larger than said absorbent core to enable folding of said envelope to juxtapose said adhesive means and said adhesive release means without folding said core, said adhesive fasteners disposed on the outside surface of said envelope adjacent a longitudinal edge thereof, whereby said garment constitutes a disposable insert adapted for securement in use within another waste containment garment.

2. A disposable waste-containment garment comprising an envelope of flexible sheet material having corners and opposite ends an absorbent core wholly enclosed within said envelope, and a plurality of adhesive fasteners which do not extend beyond the edges of said envelope each of said adhesive fasteners comprising adhesive means and adhesive-release means in side by side adjacency with each other, said envelope defining an outside surface facing away from the wearer and an inside surface facing the wearer, said envelope being folded such that prior to use each adhesive means is peelably adhered to its respective adjacent adhesive-release means whereby said envelope may be unfolded for use by peeling said adhesive means from said adhesive release means, said envelope being sufficiently larger than said absorbent core to enable folding of said envelope to juxtapose said adhesive means and said adhesive release means without folding said core, said adhesive fasteners disposed on the outside surface of said envelope at two corners of one end, whereby said garment constitutes a disposable insert adapted for securement in use within another waste containment garment.

3. The disposable waste-containment garment of claim 1 or 2 wherein each said adhesive means is spaced from said longitudinal edge of said envelope to define a grasping edge portion of said envelope intermediate said adhesive means and said longitudinal edge, said space being sufficient to enable a user to manually grip said grasping edge portion to apply an outward pull thereon to effect peeling each said adhesive means from its said respective adjacent adhesive-release means.

4. The disposable waste-containment garment of claim 1 or 2 wherein said adhesive means comprises an adhesive substrate which is adhered to said surface of said envelope and which is coated on its outwardly facing surface with pressure sensitive adhesive, and wherein said adhesive-release means comprises an adhesive-release substrate which has one face which is non-releasably adhered to said surface of said envelope and the other face of which has sufficient release property with respect to said pressure sensitive adhesive that said outwardly facing surface of said adhesive substrate may be peelably adhered to said other face of said adhesive-release substrate with said pressure sensitive adhesive.

5. The disposable waste-containment garment of claim 1 or 2 wherein said adhesive means comprises a coating of a pressure sensitive adhesive on a predetermined first portion of a said corner surface region of said envelope.

6. The disposable waste-containment garment of claim 1 or 2 wherein said means for peelably securing comprises a coating of release material disposed directly on a second portion of said corner surface region.

7. The disposable waste-containment garment of claim 6 wherein said adhesive means comprises a coating of a pressure sensitive adhesive on a predetermined first portion of a said corner surface region of said envelope.

8. The disposable waste-containment garment of claim 2 wherein said same side of said envelope is the side of said envelope which faces inwardly towards the body of a user thereof whereby said garment constitutes a disposable diaper which may be secured on a user by applying said adhesive means of said adhesive fasteners to outwardly facing surface areas of said envelope disposed at the opposite end of said garment from the end on which said adhesive fastener are disposed.

* * * * *